United States Patent [19]

Wohltjen et al.

[11] 4,078,551

[45] Mar. 14, 1978

[54] ELECTRONIC SPHYGMOMANOMETER

[76] Inventors: Henry Wohltjen, 146 Daleham St., Staten Island, N.Y. 10308; George Vachtsevanos, Polytechnic School of Xanthi, Xanthi, Greece; Robert E. King, City University of New York, St. George, Staten Island, N.Y. 10301

[21] Appl. No.: 623,059

[22] Filed: Oct. 16, 1975

[51] Int. Cl.² ............................................. A61N 5/02
[52] U.S. Cl. ............................................. 128/2.05 M
[58] Field of Search .................... 128/2.05 A, 2.05 M, 128/2.05 Q, 2.05 R; 307/220 R, 226 R

[56] References Cited

U.S. PATENT DOCUMENTS

| 3,623,476 | 11/1971 | Robillard | 128/2.05 M |
| 3,868,679 | 2/1975 | Arngson | 128/2.05 A |
| 3,893,452 | 7/1975 | Birnbaum | 128/2.05 A |

FOREIGN PATENT DOCUMENTS

| 1,197,796 | 7/1970 | United Kingdom | 128/2.05 A |

OTHER PUBLICATIONS

Fiegel, Jr. "IBM Tehcnical Disclosure Bulletin" vol. 8, No. 6, Nov. 1965, p. 871.

Primary Examiner—William E. Kamm

[57] ABSTRACT

A sphygmomanometer having an inflatable occluding cuff adapted to be applied to a patient. A pressure transducer is in fluid communication with the cuff so as to produce an electrical analog signal proportional to the actual pressure in the cuff and to superpose electrical pulses on the analog signal in response to pulsations in the patient's blood pressure during cardiac cycles. An analog-to-digital converter is coupled to the pressure transducer to produce a digital representation of the actual pressure then obtaining in the cuff. A pulse detector is coupled to the pressure transducer to detect the superposed electrical pulses. The digital representation produced by the analog-to-digital converter is displayed in response to the first-detected pulse; and the digital representation subsequently produced by the converter is displayed in response to the finally detected pulse, thereby resulting in the display of the patient's systolic and diastolic pressures, respectively.

1 Claim, 17 Drawing Figures

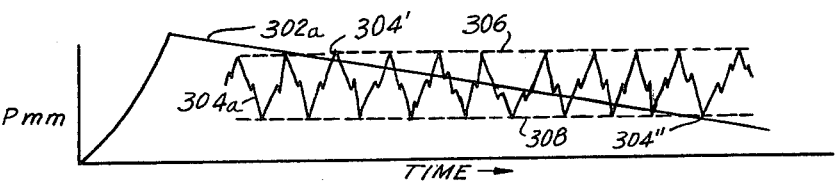
FIG.3A Pmm
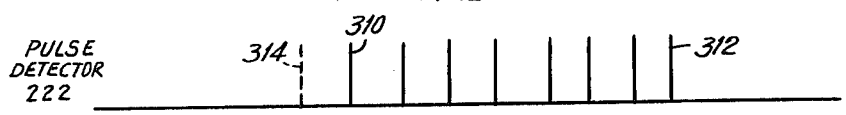
FIG.3B PULSE DETECTOR 222
FIG.3C VCO 204
FIG.3D CLOCK
FIG.3E PULSE TRAIN GATE 206
FIG.3F FF 226
FIG.3G OR 228
FIG.3H FF 242
FIG.3I FF 262
FIG.3J SYSTOLIC COUNTER
FIG.3K SYSTOLIC COUNTER RESET
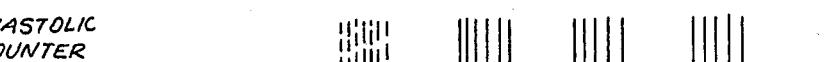
FIG.3L DIASTOLIC COUNTER
FIG.3M DIASTOLIC COUNTER RESET

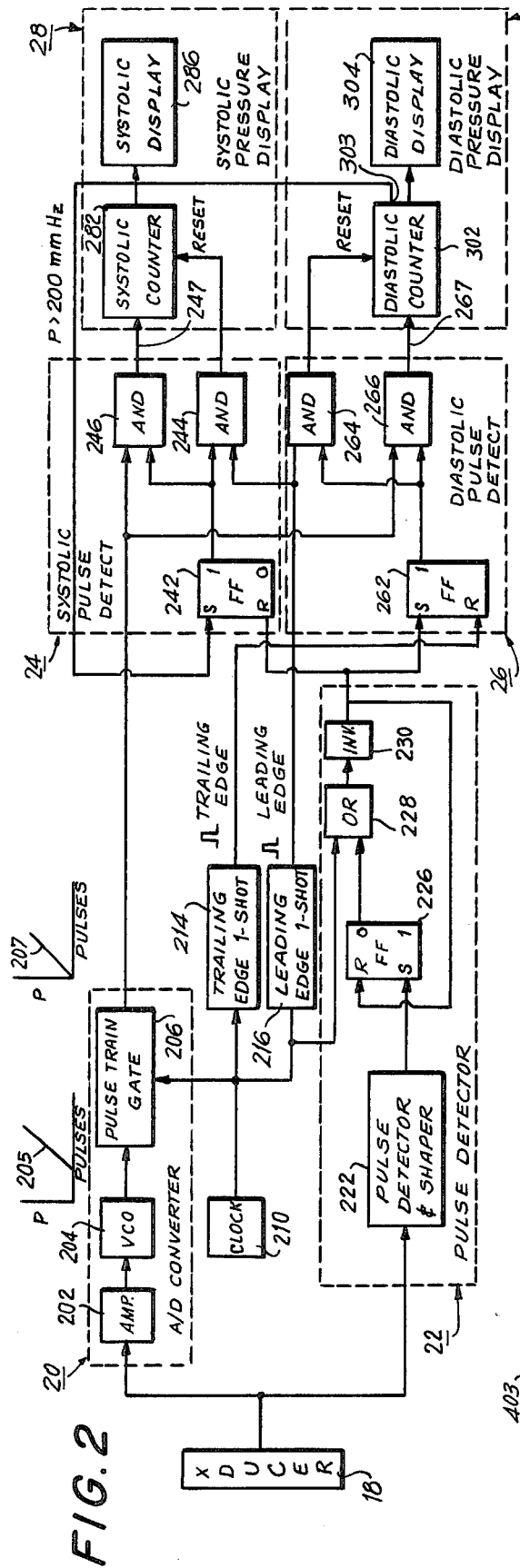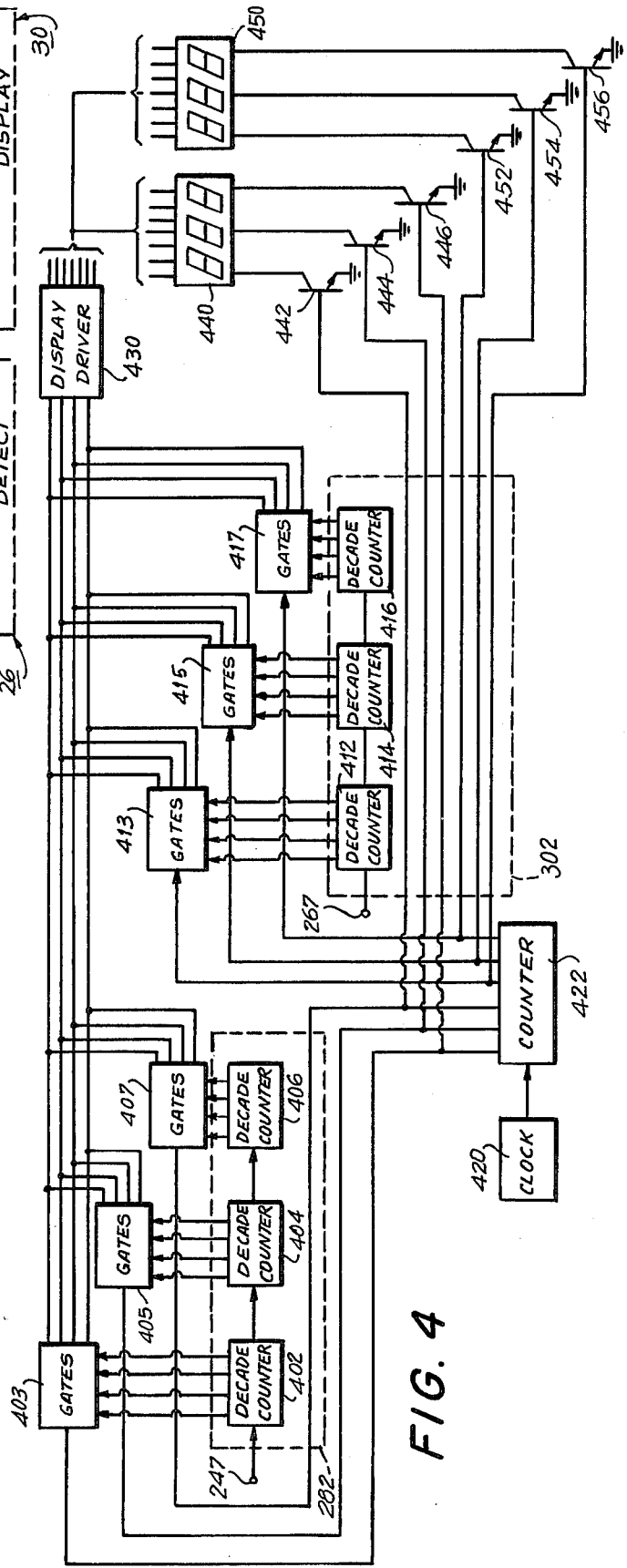
FIG. 2
FIG. 4

ELECTRONIC SPHYGMOMANOMETER

BACKGROUND OF THE INVENTION

This invention relates to an electronic sphygmomanometer and, in particular, to a sphygmomanometer wherein accurate measurement of a patient's systolic and diastolic pressures are obtained without requiring the use of a sound transducer for detecting Korotkoff sounds.

It has long been known that an approximation of a patient's systolic blood pressure and diastolic blood pressure can be obtained by detecting the so-called Korotkoff sounds. Essentially, this measurement technique utilizes an inflatable occluding cuff which usually is wrapped about a patient's limb so as to close, or completely occlude, an artery. Typically, the occluding cuff is wrapped about the arm in juxtaposition to the brachial artery. When the cuff is inflated to a pressure which exceeds the patient's systolic pressure, so as to close this artery, blood is no longer capable of flowing therethrough. As the cuff is slowly deflated, a point is reached whereat the patient's systolic pressure exceeds the cuff pressure. Consequently, the artery opens for a short period during the patient's cardiac cycle. Once the blood pressure during this cardiac cycle falls below the cuff pressure, the artery once again is closed.

The pressure in the cuff which is equal to the maximum blood pressure during a cardiac cycle is, of course, the systolic pressure. It is known that when the blood pressure exceeds the actual cuff pressure, resulting in the opening of the artery, turbulence in the blood stream is accompanied by a sound which is the so-called Korotkoff sound. These Korotkoff sounds occur each time that the artery is opened. Thus, as long as the cuff pressure exceeds the lowest, or diastolic, pressure in the cardiac cycle, the artery will be alternately opened and closed as the cardiac cycle pressure traverses the cuff pressure. When the cuff pressure falls below the lowest pressure point in the cardiac cycle, the artery will remain opened, and the Korotkoff sounds no longer will be produced. Consequently, by measuring the cuff pressure at the last Korotkoff sound, a close approximation is made of the patient's diastolic pressure.

It is common practice to deflate the cuff at a rate which is much slower than the cardiac cycle. For example, the cuff is deflated at a rate in the range of 2mm Hg per second to 4mm Hg per second; so that it is expected that a Korotkoff sound will be present for each millimeter of mercury during the cuff deflation until the diastolic pressure is reached.

To detect the Korotkoff sounds, a suitable listening device has been required. For manual measurements of blood pressure, a stethoscope is applied to the patient's arm downstream of the occluding cuff. Because of the relative insensitivity of a conventional stethoscope, and further in view of ambient noises which can cause distraction or confusion in the detection of an actual Korotkoff sound, it is necessary for a physician or an otherwise skilled technician to take blood pressure measurements. This, of course, is an inefficient and generally wasteful use of a physician's time and skill.

Accordingly, there have been previous proposals for sphygmomanometers which can be used to measure blood pressure without the assistance of a physician or a highly skilled technician. In these earlier proposals, the detection of the Korotkoff sounds are achieved automatically and the associated cuff pressure readings are derived in conjunction with the detected Korotkoff sounds by electronic apparatus. It is generally believed that, prior to the instant invention, all of the earlier proposals and systems proceeded upon the detection of the Korotkoff sounds and, therefore, required the use of a microphone. Unfortunately, the automatic detection of Korotkoff sounds is accompanied by various problems and disadvantages. For example, the characteristic Korotkoff sounds of one patient may be vastly different from those of another patient. In particular, the amplitudes of these Korotkoff sounds may differ by many orders of magnitude. As another example, in some patients, during cuff deflation, but while the cuff pressure is between the patient's systolic and diastolic pressures, the Korotkoff sounds will appear to cease but then subsequently reappear. Since the finally detected Korotkoff sound is assumed to correspond to the patient's diastolic pressure, this interruption in the Korotkoff sounds will lead to erroneous measurements. As another example, background noises, known as artifactual noise to distinguish these noises from the Korotkoff sounds, can closely approximate such Korotkoff sounds and thus will be falsely detected. Attempts to overcome these, and other, problems are described in the patent art. For example, in U.S. Pat. No. 3,405,707, it is proposed to automatically simulate the selective process for discriminating Korotkoff sounds which is used by a physician. Nevertheless, this proposal requires the use of a microphone for sensing the Korotkoff sounds. Another proposal, described in U.S. Pat. No. 3,771,515, also relies on the use of a microphone.

Although it has been known that separate pressure signals are produced generally in phase with the Korotkoff sounds during a cardiac cycle, as mentioned in U.S. Pat. No. 3,349,763, nevertheless, there has been no previous attempt to detect these pressure signals and to use them in measuring blood pressure. In fact, even though pressure transducers have been used to sense cuff pressure, as described, for example, in U.S. Pat. Nos. 3,450,131 and 3,508,537, there has been no attempt to use a pressure transducer for sensing these pressure signals and for using same to measure systolic and diastolic pressure. Rather, the classic technique which relies upon the detection of the Korotkoff sounds, as described in U.S. Pat. No. 3,371,661, has been maintained.

Unfortunately, all of these systems which require the detection of the Korotkoff sounds are accompanied by many of the foregoing problems. Attempts to avoid the disadvantages inherent in sensing the Korotkoff sounds have not been entirely successful. Although the use of digital techniques has improved the measuring sensitivities, the unreliability of sound detection has tended to substantially nullify these improvements in accuracy. Although still better results can be achieved by using highly sensitive and discriminating microphones, the consequential increases in manufacturing costs and maintenance of the sphygmomanometer do not economically justify the use of such microphones.

OBJECTS OF THE INVENTION

Therefore, it is an object of the present invention to provide an improved electronic sphygmomanometer wherein the aforenoted problems and disadvantages attending prior art devices are avoided.

It is another object of the present invention wherein an electronic sphygmomanometer is provided having no sound transducer for the detection of Korotkoff sounds.

A further object of this invention is to provide a sphygmomanometer wherein a single pressure transducer is used to detect the pressure in an occluding cuff and to detect pressure pulsations during cardiac cycles of a patient.

An additional object of this invention is to provide an improved sphygmomanometer wherein systolic and diastolic pressures of a patient are measured in accordance with digital techniques.

Yet another object of this invention is to provide a sphygmomanometer of simple and low cost construction which is capable of achieving highly accurate measurements of a patient's blood pressure.

A still further object of this invention is to provide a sphygmomanometer which admits of simplified operation so that blood pressure measurements can be taken without the assistance of a highly skilled technician.

Another object of the present invention is to provide a sphygmomanometer which can be used by a patient for measuring his own blood pressure.

Various other objects and advantages of the present invention will become apparent from the ensuing detailed description, and the novel features will be pointed out in the appended claims.

SUMMARY OF THE INVENTION

In accordance with the present invention, a sphygmomanometer is provided having an inflatable occluding cuff to be applied to a patient and including a pressure transducer for producing an electrical analog signal representative of the actual pressure in the cuff and for superposing electrical pulses on the analog signal in response to pressure pulsations during cardiac cycles of the patient; the analog signal is converted to a digital representation of the cuff pressure, and the superposed pulses are separately detected; the first detected pulse which is sensed while the cuff pressure is reduced from a maximum value is used to produce a signal representing the systolic pressure, and the final pulse which is sensed when the cuff pressure is further reduced is used to produce a signal representing the diastolic pressure; and the digital representation of cuff pressure then obtaining when the systolic pressure representing signal is produced as well as the digital representation of cuff pressure then obtaining when the diastolic pressure representing signal is produced are respectively displayed as systolic and diastolic pressures.

The digital representation of cuff pressure is produced by means of a simplified, low cost analog-to-digital converting circuit. In one embodiment thereof, this analog-to-digital converting circuit includes a voltage controlled oscillator which generates a pulse train having a pulse repetition rate which is linearly proportional to an analog signal applied thereto; the pulse train being periodically sampled during predetermined sampling intervals; and the number of pulses included in the pulse train during the sampling interval being used as a direct digital representation of the analog signal. For those oscillators wherein the pulse repetition rate is not reduced to zero even though the input analog signal level is substantially equal to zero, these zero-offset pulses are subtracted from the sampled pulse train so as to produce a resultant pulse train wherein the number of pulses is directly proportional to the analog signal level.

In accordance with a feature of the present invention, the pressure measurements are displayed by conventional multi-digit seven-segment light-emitting displays. To minimize costs, a single-digit display driver is used to drive all of the display elements. A simple multiplexing circuit is used to supply the display driver with each digit to be displayed.

In a preferred embodiment of this invention, integrated circuit techniques are used, so that the occluding cuff, control electronics and display elements all can be incorporated directly into the cuff structure. Furthermore, by sensing the pressure pulsations during a patient's cardiac cycle, rather than by detecting the Korotkoff sounds, the occluding cuff can be wrapped about any convenient limb. For example, the occluding cuff may be wrapped about a patient's upper arm to surround the brachial artery or about a patient's wrist to surround the radial artery.

BRIEF DESCRIPTION OF THE DRAWINGS

The following detailed description, given by way of example, will best be understood in conjunction with the accompanying drawings in which:

FIG. 2 is a partial block, partial logic diagram illustrating the control electronics of this invention;

FIGS. 3A–3M are waveform diagrams which are helpful in explaining the operation of the embodiment shown in FIG. 2;

FIG. 4 is a logic diagram illustrating the display apparatus which can be used with the present invention.

DETAILED DESCRIPTION OF A CERTAIN PREFERRED EMBODIMENT

Figure 1:
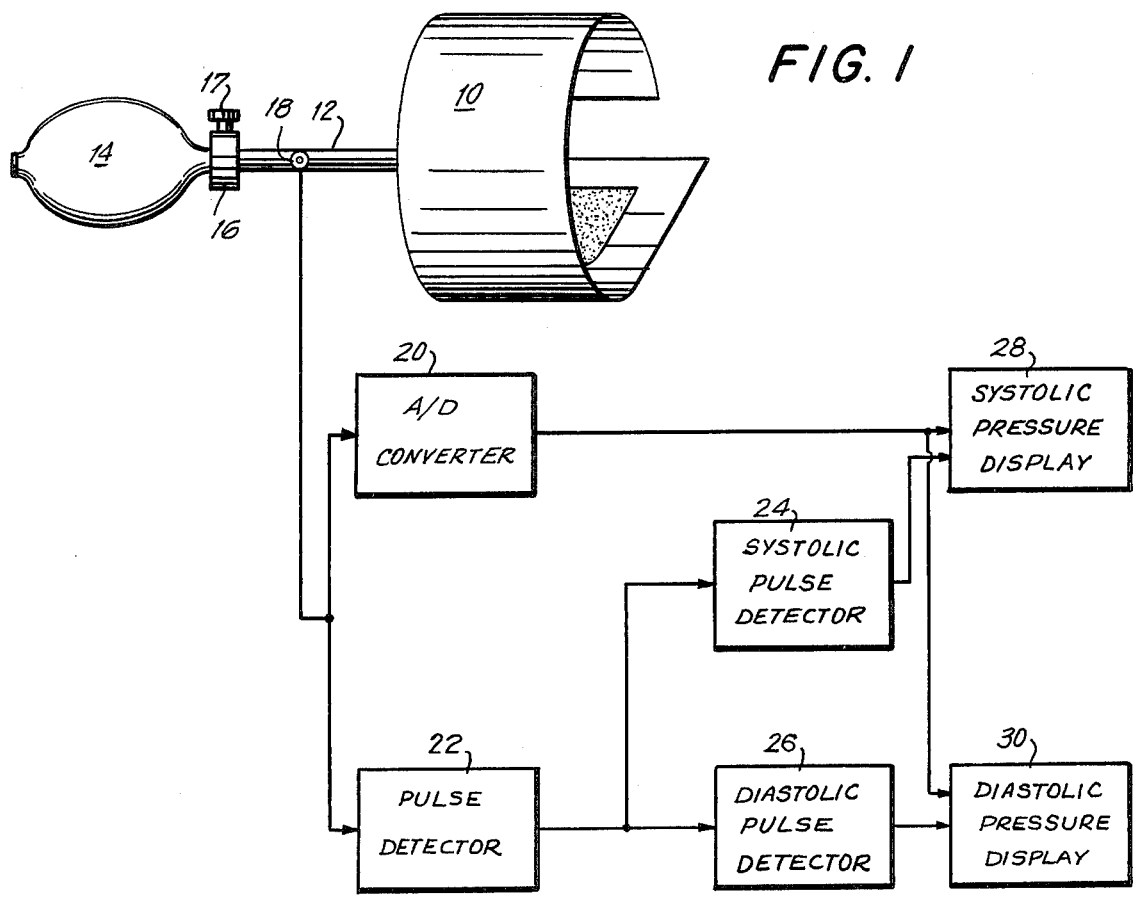
FIG. 1 is a block diagram illustrating the apparatus of the present invention.

Referring now to the drawings, wherein like reference numerals are used throughout, and in particular to FIG. 1, there is illustrated a block diagram of the apparatus which can be used with the present invention. As is conventional, the sphygmomanometer is comprised of an occluding cuff 10 which is adapted to be inflated by receiving a fluid, such as air, applied thereto by a pressure hose 12. The occluding cuff 10 may be wrapped about any convenient limb of a patient, such as the upper arm to surround the brachial artery. Alternatively, the occluding cuff may be wrapped around a patient's wrist. Suitable fastening members, not shown, are used to maintain the cuff in stable position during inflation and during pressure measurement.

In one embodiment, the occluding cuff 10 is manually inflated by the usual technique of squeezing a bulb member 14. Fluid pulses applied from the bulb 14 through the hose 12 to the cuff 10 can be smoothed by a suitable regulator valve, an air chamber, or the like. For the present discussion, it will be assumed that a regulating valve 16 is provided for this purpose and the cuff 10 is subjected to a relatively rapid and smooth inflation. As is also conventional, the cuff 10 is adapted to be deflated by the suitable control of an escape valve 17.

A pressure transducer 18 is positioned in fluid communication with the cuff 10 and is adapted to produce an electrical analog signal which is representative of the cuff pressure. As is apparent, the pressure transducer 18 may be placed within the cuff or, as shown, the transducer may be positioned in the pressure hose 12. Notwithstanding the specific location of the pressure transducer 18, the transducer is further adapted to detect the smoothed fluid pulses applied during cuff inflation and pressure pulsations in the occluded artery of the patient, and to superpose electric pulses on the analog signal in response to these pressure pulsations. As will be described in greater detail hereinbelow with respect to FIG. 3A, it is known that a pressure pulsation will occur during a cardiac cycle when the patient's pressure, which varies from a systolic peak to a diastolic peak, traverses the cuff pressure. Accordingly, when the pressure fluctuation in a cardiac cycle exceeds the pressure of the occluding cuff 10, the pressure transducer 18 serves to superpose an electrical pulse on the cuff pressure-representing analog signal. A typical pressure transducer which may be used with this invention is produced by National Semiconductor Corporation of Santa Clara, California and is identified as Model LX1600 or LX1700. Another type of pressure transducer which can be used is manufactured by Stow Laboratories, Inc. of Hudson, Massachusetts, and is identified as the Pitran Pressure Transistor.

As illustrated, the output of the pressure transducer 18 is coupled in common to an analog-to-digital converter 20 and to a pulse detector 22. The analog-to-digital converter 20 is adapted to convert the analog signal representing the cuff pressure to a digital representation. As the cuff pressure changes, the digital representation produced by the analog-to-digital converter 20 likewise changes.

The pulse detector 22 is adapted to sense the superposed pulses produced by the pressure transducer 18 and to shape these pulses into desirable form. The output of the pulse detector 22 is coupled in common to a first pulse detector 24, designated the systolic pulse detector, and to a second pulse detector 26, designated the diastolic pulse detector. As will be described in greater detail below, the systolic pulse detector 24 is adapted to sense the first pulse which is detected by the pulse detector 22. It is appreciated that the first pulse which is detected by the pulse detector 22 is produced when the pressure in the occluding cuff 10 is equal to or slightly less than the patient's systolic pressure. The diastolic pulse detector 26 is adapted to sense the final pulse which is detected by the pulse detector 22. It is appreciated that when the pressure in the cuff 10 is equal to or slightly greater than the patient's diastolic pressure, a pulse will be produced by the pressure transducer 18. However, when the cuff pressure falls below the patient's diastolic pressure, no further pulses will be produced by the transducer. Thus, the last, or final, pulse produced by the transducer 18 and detected by the pulse detector 22 is sensed by the diastolic pulse detector 26.

A systolic pressure display 28 and a diastolic pressure display 30 are coupled in common to the analog-to-digital converter 20 and are adapted to receive and display the digital representations produced by the converter. In addition, the systolic pressure display 28 is coupled to the systolic pulse detector 24; and the diastolic pressure display 30 is coupled to the diastolic pulse detector 26. In a preferred embodiment of this invention, the respective displays are optical displays formed, for example, by multi-digit light-emitting elements. As is conventional in the art, the pressure is measured and indicated in the form of millimeters of mercury. Consistent with this convention, the displays 28 and 30 preferably provide indications of systolic and diastolic pressure in millimeters of mercury.

In one embodiment thereof, the systolic pressure display 28 is responsive to a signal applied thereto by the systolic pulse detector 24 when the detector 24 senses the first pulse which is detected by the pulse detector 22, to thereby display the multi-digit number which is digitally represented by the output of the analog-to-digital converter 20. That is, as the digital representation produced by the converter 20 changes while the cuff 10 is deflated from a maximum pressure, the pressure representation produced by the converter is not displayed until the systolic pressure display 28 is actuated by the signal produced by the systolic pulse detector 24. At that time, the pressure then obtaining in the cuff 10 closely approximates the patient's systolic pressure, and the digital representation of this cuff pressure is stored and displayed in the systolic pressure display 28. Further changes in the digital representation produced by the analog-to-digital converter 20 will not affect the data now stored in and displayed by the display 28.

In an alternative embodiment, the systolic pressure display 28 normally is actuated so as to display the multi-digit representation of cuff pressure which is produced by the analog-to-digital converter 20. Hence, as the cuff pressure changes, for example, during cuff deflation, the systolic pressure display 28 likewise changes. Now, when the systolic pulse detector 24 senses the first pulse which is detected by the pulse detector 22, a signal is supplied to the systolic pressure display 28 to disable that display from responding to further changes in the digital representation supplied by the converter 20. Consequently, the last indication of cuff pressure which is displayed by the systolic pressure display 28 will be retained thereby once the initial pulse produced by the pressure transducer 18 is detected.

The diastolic pressure display 30 is substantially similar to the systolic pressure display 28 and operates in a similar manner. Hence, in one embodiment, it is appreciated that the display 30 does not respond to the digital representation of cuff pressure supplied thereto until the diastolic pulse detector 26 senses the final pulse which is detected by the pulse detector 22 and supplies an actuating signal to the diastolic pressure display 30. At that time, the digitized representation of the then obtaining cuff pressure will be supplied to and displayed by the display 30. In the alternative embodiment, the pressure indication displayed by the display 30 will be changed, or up-dated, as the output of the analog-to-digital converter 20 is changed. The diastolic pressure display 30 is inhibited from responding to further changes in the digital representation supplied by the converter 20 once the diastolic pulse detector 26 senses the final pulse which is detected by the pulse detector 22. Thus, it is seen that further deflation of the cuff 10 does not disturb the pressure measurement indications displayed by the systolic and diastolic pressure displays 28 and 30, respectively.

While the foregoing has assumed that the cuff 10 is inflated by squeezing the bulb 14 in conventional manner, it is recognized that alternative inflating devices may be used, if desired. For example, a suitable pump or compressor can be used to supply fluid under pressure to the cuff 10. As a further alternative, canisters of compressed gas may be used. Once the cuff 10 has been inflated to a desirable pressure, i.e., to a pressure well above the systolic pressure of the patient, the escape valve 17 may be manually operated so as to slowly deflate, or bleed, the cuff. It should be understood that, if desired, automatic deflating mechanisms may be used. In that event, when the cuff pressure exceeds a desirable threshold, as indicated by the pressure transducer 18 and/or the analog-to-digital converter 20, the automatic deflating mechanism can be actuated. This pressure threshold can be determined in accordance with the physiological characteristics of a patient or, alternatively, may be set at a level which is not expected to be exceeded by a patient's systolic pressure. As one example, this threshold can be selected at 200mm Hg.

The block diagram of the electronic apparatus shown in FIG. 1 is depicted in greater detail in the partial block, partial logic diagram of FIG. 2. As shown therein, the pressure transducer 18 is coupled to the analog-to-digital converter 20 which is comprised of a voltage controlled oscillating circuit 204 coupled to a pulse train gating circuit 206. The voltage controlled oscillating circuit 204 may be conventional, and as is known, has an oscillating frequency which is proportional to an analog signal applied thereto. Accordingly, an amplifying stage 202 may be used to supply the analog signal produced by the transducer 18 to the voltage controlled oscillating circuit 204.

It is preferred that the voltage controlled oscillating circuit 204 produce a pulse train whose pulse repetition rate is directly proportional to the pressure-representing analog signal applied thereto. Thus, desirably, if the pressure is equal to 0mm Hg, the pulse repetition rate likewise should be zero pulses per second (pps). Similarly, when the pressure is equal to 200mm Hg, the pulse repetition rate should be K times 200 pps, where K is an integer. However, it has been found that, with many commercially available voltage controlled oscillating circuits, the pulse repetition rate is not reduced to zero even though the input analog signal applied thereto is substantially equal to zero. This characteristic feature of such a voltage controlled oscillating circuit is graphically represented by the curve 205. It is recognized that if the pressure P is reduced to zero, zero offset pulses are produced. However, as the pressure P is increased, the pulse repetition rate is directly proportional to, and thus linearly increases with, the pressure. The pulse train gating circuit 206, coupled to the output of the voltage controlled oscillating circuit 204, is adapted to remove the zero offset pulses, whereby the curve 205 is effectively shifted so as to intersect the origin, as shown in the curve 207.

Figure 5:
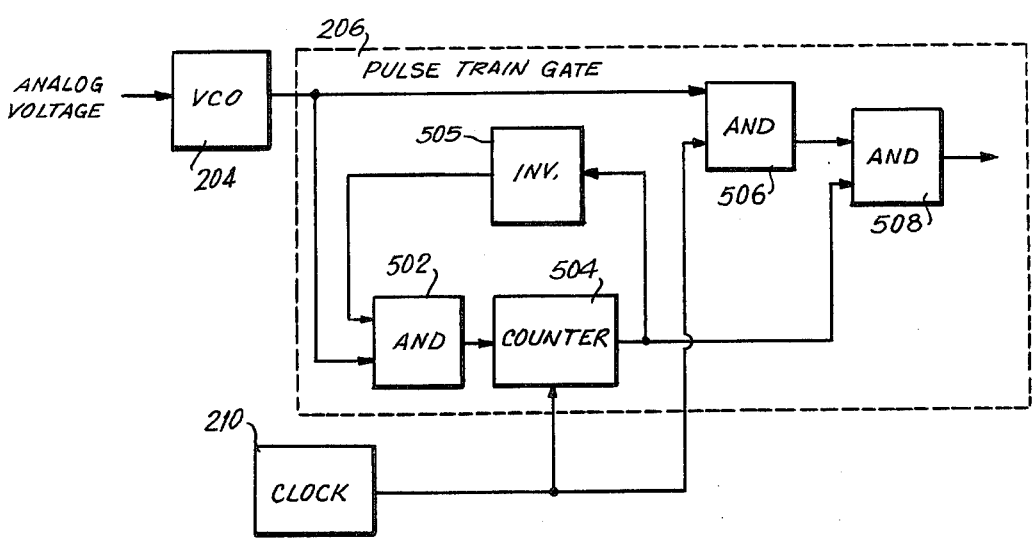
FIG. 5 is a logic diagram illustrating the analog-to-digital converter which can be used with this invention.

As will be described in greater detail with reference to FIG. 5, the pulse train gating circuit 206 is adapted to periodically sample a portion of the pulse train produced by the voltage controlled oscillating circuit 204, and to transmit this sampled portion to further apparatus. The number of pulses included in this sampled portion of the pulse train is directly proportional to the cuff pressure, as sensed by the pressure transducer 18. The zero offset pulses attending the operation of the voltage controlled oscillating circuit 204 are removed from the sampled portion of the pulse train. A clock circuit 210 is coupled to the pulse train gating circuit 206 and is adapted to produce a periodic sampling pulse having a predetermined sampling interval. Therefore, it should be readily appreciated that if the number of pulses included in the sampled portion of the pulse train corresponds to the cuff pressure in millimeters of mercury, an indication of the cuff pressure can be readily attained merely by counting the number of pulses transmitted during a sampling interval.

The pulse detecting circuit 22 is coupled to the pressure transducer 18 and comprises a pulse detecting and shaping circuit 222, a bistable multivibrator 226 (hereinafter a flip-flop circuit) and an OR circuit 228. The pulse detecting and shaping circuit 222 is adapted to detect the superposed pulses which are produced by the transducer 18. Accordingly, this circuit may comprise a conventional amplifying stage, together with filter and differentiating circuits which are well known to those of ordinary skill in the art. Hence, the pulse detecting and shaping circuit 222 is adapted to produce an output pulse that is relatively free of noise and which exhibits a desirable amplitude and duration.

The flip-flop circuit 226 is conventional and admits of two stable states. In the illustrated embodiment, this flip-flop circuit may comprise a R-S flip-flop having a set input terminal coupled to the pulse detecting and shaping circuit 222 and a reset input terminal coupled through an inverting circuit 230 to the OR circuit 228. For the purpose of the present discussion, it will be assumed that the flip-flop circuit is adapted to be set, or actuated, to its first, or "set" state when a binary "1" is applied to the set input terminal. Conversely, the flip-flop circuit is adapted to be reset, or actuated, to its second, or "reset" state when a binary "1" is applied to the reset input terminal. Consistent with this assumption, it will be further assumed that a binary "1" is represented by a positive DC level, whereas a binary "0" is represented by a lower DC level. More particularly, the binary "0" may be represented by a negative DC level or by ground potential. As is understood, when the flip-flop circuit 226 is in its "set" state, a binary "1" is produced at the 1 output terminal and a binary "0" is produced at the 0 output terminal. Conversely, when the flip-flop circuit is in its "reset" state, a binary "0" is produced at the 1 output terminal and a binary "1" is produced at the 0 output terminal.

Although the foregoing convention of designating binary signals will be used throughout this discussion, it should be readily understood that various other representations and compatible devices can be used, if desired. Thus, a binary "1" can be represented by a ground potential and a binary "0" can be represented by a higher, positive potential. Also, signals of negative polarity can be used.

It will soon become apparent that the flip-flop circuit 226 is adapted to be set to its "set" state in response to each pressure pulse which is detected by the pulse detecting and shaping circuit 222. The flip-flop circuit is adapted to be reset to its "reset" state during those clock intervals when a pulse train produced by the voltage controlled oscillator 204 is not sampled. Accordingly, the reset circuit of the flip-flop circuit 226 is formed of the OR circuit 228 which includes a first input terminal coupled to the zero output terminal of the flip-flop circuit and a second input terminal adapted to be supplied with the clock pulses produced by the clock circuit 210. As is known, an OR circuit is a logic element which is adapted to produce a binary "1" at its output terminal when a binary "1" is supplied to any input terminal thereof. A binary "0" is produced by an OR circuit only if each input terminal is supplied with a binary "0". The output terminal of the OR circuit 228 is coupled to the reset input terminal of the flip-flop circuit 226 by the inverting circuit 230. The inverting circuit is adapted to invert the logical sense of the binary signal produced by the OR circuit. Hence, a binary "1" is inverted to a binary "0" and, conversely, a binary "0" is inverted by the inverting circuit to a binary "1".

The inverting circuit 230 is further coupled in common to the systolic pulse detecting circuit 24 and to the diastolic pulse detecting circuit 26. The systolic pulse detecting circuit is comprised of a flip-flop circuit 242, an AND-gate 244 and an AND-gate 246. The flip-flop circuit 242 is similar to the aforedescribed flip-flop circuit 226 and, therefore, may comprises a R-S flip-flop. As shown, the reset input terminal of the flip-flop circuit 242 is coupled to the inverting circuit 230. The set input terminal of the flip-flop circuit 242 is coupled to a predetermined stage of a counter circuit 302 included in the diastolic pressure display 30 for a purpose to become apparent. At the present time, it merely may be noted that the flip-flop circuit 242 is adapted to be set to its "set" state when the counter circuit 302 is incremented to a predetermined count, and is adapted to be reset to its "reset" state immediately following the sensing by the pulse detecting and shaping circuit 222 of the first pressure pulse.

The 1 output terminal of the flip-flop circuit 242 is connected in common to respective input terminals of the AND-gates 244 and 246. As is known, an AND-gate is a conventional coincidence circuit of the type wherein a binary "1" is produced at its output only when a binary "1" is supplied to each input terminal. The AND-gate produces a binary "0" when a binary "0" is applied to any input terminal.

The output terminal of the AND-gate 244 is coupled to the counter circuit 282 and is adapted to supply a reset signal thereto. To this effect, the AND-gate 244 includes a second input terminal which is connected to the clock circuit 210 by a monostable multivibrator circuit 216. The monostable multivibrator circuit 216 is a conventional one-shot circuit capable of producing a pulse of predetermined duration in response to a positive transition applied thereto. Thus, the one-shot circuit 216 supplies relative narrow pulses to the AND-gate 244 at each leading edge of a clock pulse.

The AND-gate 246 is adapted to transmit the sampled pulse train produced by the pulse train gating circuit 206 to the counter circuit 282. Accordingly, the other input terminal of the AND-gate 246 is connected to the pulse train gating circuit 206 and the output terminal of the AND-gate is connected to the counter circuit 282. It may be appreciated that when the flip-flop circuit 242 is in its "set" state, the AND-gate 246 is enabled to transmit the sampled pulse trains to the counter circuit. However, once the flip-flop circuit 242 is reset to its "reset" state, the AND-gate 246 is disabled from transmitting further pulses to the counter circuit. As will soon become apparent, the resetting of the flip-flop circuit 242 is partially controlled by the clock circuit 210 so as to avoid a premature disabling of the AND-gate 246, and thereby avoiding the possibility of transmitting only an incomplete portion of the sampled pulse train.

The diastolic pulse detecting circuit 26 is comprised of a flip-flop circuit 262 and first and second AND-gates 264 and 266, respectively. The flip-flop circuit 262 is similar to the aforedescribed flip-flop circuit 242 and includes a set input terminal coupled to the inverting circuit 230 and a reset input terminal coupled to the clock circuit 210 by a monostable multivibrator circuit 214. This multivibrator circuit comprises a conventional one-shot circuit for producing a positive pulse of predetermined duration in response to a negative transition applied thereto. Thus, the one-shot circuit 214 is adapted to produce output pulses upon detecting the trailing edges of the clock pulses supplied by the clock circuit 210. As an alternative embodiment thereof, the one-shot circuit 214 may be substantially identical to the one-shot circuit 216, i.e., it may produce an output pulse in response to a positive transition applied thereto, and an inverting circuit, not shown, may be used to connect the clock circuit 210 to the one-shot circuit 214.

The 1 output terminal of the flip-flop circuit 262 is connected in common to respective input terminals of the AND-gates 264 and 266. The AND-gate 264 is adapted to supply reset pulses to a counter 302 included in the diastolic pressure display 30. To this effect, the other input terminal of the AND-gate 264 is connected to the aforementioned one-shot circuit 216, and the output terminal of the AND-gate 264 is connected to a reset terminal of the counter 302.

The AND-gate 206 is adapted to transmit the sampled pulse trains produced by the pulse train gating circuit 206 to the counter circuit 302. Accordingly, the other input terminal of the AND-gate 266 is connected to the pulse train gating circuit 206, and the output terminal of this AND-gate is connected to a counter input terminal of the counter circuit 302. It is appreciated that the AND gate 266 is enabled to transmit the sampled pulse trains only when the flip-flop circuit 262 is in its "set" state. It will be recognized that the flip-flop circuit 262 is set to its "set" state when a pressure pulse is sensed by the pulse detecting and shaping circuit 222 and is reset to its "reset" state at the conclusion of a sampling interval. In this manner, a complete sampled portion of the pulse train is transmitted to the counter circuit 302 so long as the pressure pulses are sensed.

The systolic pressure display 28 is comprised of the counter circuit 282, designated the systolic counter, and display elements 286, designated the systolic display. The systolic counter 282 may comprise any conventional counting circuit such as a binary counter, a BCD counter, a decade counter, or the like. In the preferred embodiment, the systolic counter 282 is incremented in response to each pulse transmitted thereto by the AND-gate 246. As is known, the contents of a decade counter remain unchanged until the counter is subsequently incremented or until the counter is cleared, or reset.

Preferably, the systolic counter 282 is comprised of three cascaded decade counters which are adapted to count in decimal form the pulses applied thereto. The decimal count attained by the systolic counter 282 is supplied to and displayed by the systolic display 286. If the systolic display 286 is comprised of three seven-segment display elements, it is appreciated that a three-digit number corresponding to cuff pressure will be stored in the systolic counter 282 and directly displayed by the systolic display 286. Of course, depending upon the construction of the systolic counter 282, suitable gating and converting circuits may be used to produce a numerical display corresponding to the number of pulses which are supplied to the counter.

The diastolic pressure display 30 is comprised of the counter 302, designated a diastolic counter, and a display 304, designated a diastolic display. As described above, a predetermined stage 303 of the diastolic counter 302 is connected to the set input of the flip-flop circuit 242. Thus, when the diastolic counter is incremented to a particular count, a binary "1" is produced by the stage 303 and is supplied to the flip-flop circuit 242. The diastolic counter and display are substantially identical to the aforedescribed systolic counter and display and, in the interest of brevity, further description thereof need not be provided.

The operation of the apparatus illustrated in FIG. 2 now will be described in conjunction with the waveform diagrams shown in FIGS. 3A–3M. Let it be assumed that the cuff 10 is inflated to a maximum pressure, as indicated in FIG. 3A. During inflation, fluid pulses to the cuff are detected by the pulse detecting and shaping circuit 222 to set the flip-flop circuit 226 to its "set" state. As will be described, this sets the flip-flop circuit 262 to its "set" state so as to enable the AND-gate 266 to transmit pulse train pulses to the diastolic counter 302. Now, when maximum cuff pressure is attained, the artery surrounded by the occluding cuff 10 is closed. Also, it may be recognized that as the analog signal produced by the pressure transducer 18 increases in accordance with the cuff inflation, the oscillating frequency of the voltage controlled oscillating circuit 204 likewise increases. Hence, the number of pulses included in the sampled portion of the pulse train, as produced by the pulse train gating circuit 206, is relatively large. These pulses are transmitted by the AND-gate 266 to the diastolic counter 303 so that, when the maximum pressure level is reached, the stage 303 supplies a binary "1" to the set input terminal of the flip-flop circuit 242, thereby setting this flip-flop circuit to its "set" state. Hence, the AND-gates 244 and 246 are enabled to transmit reset pulses as well as pulse train pulses to the systolic counter 282.

After the maximum pressure in the occluding cuff 10 is reached, the cuff then is slowly deflated, as indicated by the pressure curve 302a of FIG. 3A. As this pressure decreases, the pulse repetition rate of the voltage controlled oscillating circuit 204 likewise decreases, as shown in FIG. 3C. Of course, the clock circuit 210 produces a constant, periodic clock pulse of the type shown in FIG. 3D. Each clock pulse interval is assumed to have a width T which, it is recognized, is equal to the pulse train sampling interval. Hence, the output of the pulse train gating circuit 206 is shown in FIG. 3E. The cross-hatched area in FIG. 3E represents the zero offset pulses which are subtracted from the sampled pulse train, as described above. Therefore, the total number of pulses included in the sampled pulse train, shown in FIG. 3E, is directly proportional to the pressure then obtaining in the occluding cuff.

As shown in FIG. 3A, cardiac cycles 304a are superimposed over the pressure curve 302a. These cardiac cycles represent pressure pulsations in a patient and range from a maximum systolic pressure 306 to a minimum diastolic pressure 308. Let it be assumed that the cardiac cycle first exceeds the pressure curve 302a at the point 304'. Consequently, a pressure pulse will be sensed by the transducer 18 and an electrical pulse will be superposed on the analog signal level. After detection and shaping by the pulse detecting and shaping circuit 222, this initially sensed pulse 310 will appear as shown in FIG. 3B. From this point on, it is seen that the cardiac cycles 304a traverse the pressure curve 302a during both the rising and falling portions of the cardiac cycle. However, pressure pulses will be produced only at positive transitions and the pulse detecting and shaping circuit 222 will sense these pressure pulses as shown in FIG. 3B. The last intersection between the pressure curve 302a and the cardiac cycles 304a occurs at 304". At this point, the pulse detecting and shaping circuit 222 produces the final pulse 312. Since subsequent cardiac cycles exceed the cuff pressure, no further pressure pulses will be sensed and the pressure transducer 18 will not superpose any further pulses on the analog signal level. This is depicted by the absence of pulses following the pulse 312 in FIG. 3B.

The first pulse 310 which is sensed by the pulse detecting and shaping circuit 222 serves to set the flip-flop circuit 226 to its "set" state, as shown in FIG. 3F. At this time, a positive clock pulse is present, resulting in a binary "1" supplied through the OR circuit 228 to the inverting circuit 230, as shown in FIG. 3G. Hence, the combination of the OR circuit and the inverting circuit is not capable of resetting the flip-flop circuit 226. Also, since the output produced by the inverting circuit 230 is a binary "0", it is appreciated that the flip-flop circuit 242 remains in its "set" state and the flip-flop circuit 262 remains in its "reset" state.

Now, upon the termination of the positive clock pulse, a binary "0" is applied to each input terminal of the OR circuit 228, resulting in a binary "0" supplied to the inverting circuit 230, whereat the binary "0" is inverted. At this time, the flip-flop circuit 226 is reset, as is the flip-flop circuit 242. This is shown in FIG. 3H. Prior to the resetting of the flip-flop circuit 242, it is appreciated that the sampled pulse trains shown in FIG. 3E are transmitted through the AND-gate 246 to the systolic counter 282, as shown in FIG. 3J. Also, immediately prior to the transmission of the sampled pulse train, the AND-gate 244 is enabled to transmit the clock pulse leading edge pulses produced by the one-shot circuit 216 to the reset terminal of the systolic counter 282. Thus, immediately before receiving each succeeding sampled pulse train, the systolic counter 282 is reset to an initial, or zero, count. Therefore, it is seen that, while the flip-flop circuit 242 remains in its "set" state, the systolic counter 282 periodically receives representations of the actual pressure then obtaining in the occluding cuff 10. However, once the flip-flop circuit 242 has been reset, the AND-gates 244 and 246 now are disabled. Consequently, the periodic reset pulses no longer are applied to the systolic counter 282, as shown in FIG. 3K. Also, the periodic sampled pulse trains no longer are supplied to the systolic counter, as shown in FIG. 3J. Hence, the last-received sampled pulse train shown in FIG. 3J is stored in the systolic counter. Therefore, it is fully appreciated that the count of the systolic counter 282 is periodically updated so as to represent the deflating pressure in the occluding cuff until the first pulse 310, which is produced by the pressure transducer 18 and is sensed by the pulse detecting and shaping circuit 222, occurs. Then, the last-received count, or pressure indication, is retained by the systolic counter 282 until a subsequent pressure-measuring operation is performed.

As the count stored by the systolic counter 282 is periodically updated in response to the deflating occluding cuff, the pressure measurement represented by this count is displayed by the systolic display 286. In one embodiment, the display 286 provides indications of each updated count stored by the counter 282 until the contents thereof no longer are changed, as described above. Alternatively, the display 286 can be actuated so as to provide an indication only of the last count stored by the counter 282. It is appreciated that this can be achieved by using the resetting of the flip-flop circuit 242 as a display actuating signal.

It is appreciated that, although the flip-flop circuit 242 remains in its "reset" state until a subsequent pressure measuring operation, i.e., until the diastolic counter 302 is incremented at least until the predetermined count is reached so that a binary "1" is supplied to the set input terminal of the flip-flop circuit by the stage 284, nevertheless the diastolic pressure measuring apparatus continues to operate. Pressure pulses which occur when the cardiac cycle curve traverses the pressure curve are sensed by the pressure transducer 18 and the pulses superposed on the pressure representing analog signal are supplied to the pulse detecting and shaping circuit 222. These superposed pulses, as detected by the pulse detecting and shaping circuit 222, are shown in FIG. 3B. Also, the clock circuit 210 continues to operate and the positive and negative transitions thereof, i.e., the clock pulse leading and trailing edges, are sensed by the respective one-shot circuits 216 and 214. Corresponding transition-sensing pulses are produced by these one-shot circuits.

Let it be assumed that the second pressure pulse occurs during a negative portion of a clock cycle, as shown by comparing FIGS. 3B and 3D. It is recalled that the flip-flop circuit 226 had been reset immediately following the preceding clock pulse trailing edge. Accordingly, when the next pulse is sensed by the pulse detecting and shaping circuit 222, the flip-flop circuit 226 is set to its "set" state. Since this is assumed to occur during the negative portion of a clock cycle, the OR circuit 228 now is supplied with a binary "0" at each of its input terminals resulting in a binary "0" which is inverted by the inverting circuit 230 to a binary "1". This, of course, has no effect upon the flip-flop circuit 242. However, this binary "1" is effective to immediately reset the flip-flop circuit 226 to its "reset" state and to set the flip-flop circuit 262 to its "set" state. Of course, when the flip-flop circuit 226 is reset, the 0 output terminal thereof now applies a binary "1" to an input terminal of the OR circuit 228, thus causing the inverting circuit 230 to produce a binary "0".

The aforedescribed operation produces a relatively narrow positive pulse at the 1 output terminal of the flip-flop circuit 226 and a relatively narrow negative pulse at the output terminal of the OR circuit 228, as shown in FIGS. 3F and 3G, respectively.

Now, once the flip-flop circuit 262 is set, the AND-gates 264 and 266 which are connected to the 1 output terminal of the flip-flop circuit are enabled to transmit pulses that are applied to their respective other input terminals. Thus, when the clock circuit 210 produces a positive clock pulse, the leading edge of this pulse triggers the one-shot circuit 216 to transmit a diastolic counter reset pulse through the now-enabled AND gate 264, as shown in FIG. 3M. Hence, the diastolic counter 302 is reset to an initial, or zero, count.

Immediately following the occurence of this diastolic counter reset pulse, the sampled pulse train, shown in FIG. 3E, is transmitted through the enabled AND-gate 266 to thus increment the diastolic counter 302. This is shown in FIG. 3L. Accordingly, it is seen that the cuff pressure then obtaining during the first full clock pulse interval T following the occurrence of the first pressure pulse 310 is stored in the counter 302.

When this clock pulse interval terminates, the trailing edge of the clock pulse is sensed by the one-shot circuit 214, which applies a reset pulse to the flip-flop circuit 262. Consequently, the flip-flop circuit 262 is reset to its "reset" state, as shown in FIG. 3I, and is prepared to respond to a subsequent pressure pulse.

It is appreciated that those pressure pulses which occur when the flip-flop circuit 262 admits of its "set" state have no effect thereon. Even though these pulses cause the flip-flop circuit 226 to be set to its "set" state, as shown in FIG. 3F, with the result that corresponding negative pulses are produced by the OR circuit 228, as shown in FIG. 3G, such pulses do not change the state of the flip-flop circuit 262.

However, if a pressure pulse is sensed by the pulse detecting and shaping circuit 222 during a clock pulse interval T, then the flip-flop circuit 226 will be set to its "set" state during at least a portion of this interval, with the result that, at the conclusion of the clock pulse interval, a negative pulse will be produced by the OR circuit 228, thus setting the flip-flop circuit 262 to its "set" state, immediately following the resetting thereof. This is shown in FIG. 3I. Therefore, it is appreciated that, so long as successive pressure pulses are detected, the flip-flop circuit 262 is periodically set to its "set" state, and remains in that "set" state for at least a complete clock pulse interval T. Consequently, the AND-gate 266 is periodically enabled to transmit a complete sampled portion of the pulse train, as shown in FIG. 3L. Thus, it is seen that the continued sensing of pressure pulses results in the periodic updating of the pressure-representing data stored in the diastolic counter 302.

The foregoing operation is repeated until the final pressure pulse, shown as the pulse 312 in FIG. 3B, is sensed. Let it be assumed that the final pulse 312 is sensed during a negative portion of the clock cycle shown in FIG. 3D. Hence, it is appreciated that the flip-flop circuit 226 is set to its "set" state, resulting in a negative transition at the output terminal of the OR circuit 228, as shown in FIG. 3G. This negative transition, of course, causes the flip-flop circuit 226 to be reset, with the result that the output produced at the 1 output terminal of the flip-flop circuit 226 is a relatively narrow positive pulse, and the output produced at the output terminal of the OR circuit 228 is a relatively narrow negative pulse.

It is appreciated that the flip-flop circuit 262 had been set to its "set" state following the immediately preceding trailing edge of a previous clock pulse. That is, as shown in FIGS. 3D, F and I, the flip-flop circuit 226 had been in its "set" state, due to a preceding pressure pulse, at the occurrence of the clock pulse trailing edge. This, of course, caused the OR circuit 228 to produce a relatively narrow negative pulse upon the occurrence of the clock pulse trailing edge, as shown in FIG. 3G. Hence, the flip-flop circuit 262 had been set to its "set" state. Consequently, the occurrence of the final pressure pulse 312, which also causes the OR circuit 228 to produce a relatively narrow negative pulse, has no effect upon the state assumed by the flip-flop circuit 262, as shown in FIG. 3I. That is, upon the occurrence of the immediately preceding leading edge of the clock pulse, the counter reset pulse produced by the one-shot circuit 216 is transmitted through the enabled AND-gate 264 to reset the diastolic counter 302. Following this counter reset pulse, and during the remainder of the clock pulse interval T, the sampled portion of the pulse train, shown in FIG. 3E, is transmitted through the enabled AND-gate 266, as shown in FIG. 3L, to thus increment the diastolic counter 302. At the conclusion of this clock pulse interval, the trailing edge of the clock pulse resets the flip-flop circuit 262 to its "reset" state, in the now-understood manner. This, of course, disables the AND-gates 264 and 266 from transmitting further pulses to the diastolic counter 302.

Since no additional pressure pulses are produced, the pulse detecting and shaping circuit 222 does not supply further pulses to the flip-flop circuit 226. Hence, the flip-flop circuit 226 remains in its "reset" state. As a consequence thereof, the OR circuit 228 is not capable of producing any further negative pulses. Thus, the flip-flop circuit 262 remains in its "reset" state. Therefore, it is seen that the contents of the diastolic counter 302 no longer are updated. That is, the final pressure then obtaining in the occluding cuff 10 during the clock period in which the final pressure pulse is sensed will be stored as the digital representation in the counter 302.

The contents of the diastolic counter 302 are indicated, preferably in millimeters of mercury, by the diastolic display 304. In one embodiment, the diastolic display 304 provides an indication of each count stored in the diastolic counter 302. Hence, as the contents of the diastolic counter are updated, a corresponding change is obtained in the diastolic display. In an alternative embodiment, the diastolic display 304 is actuated only when the final count is stored in the diastolic counter 302. This can be achieved by sensing whether the flip-flop circuit 262 is subsequently set to its "set" state within a predetermined time period. If such change in state has not occurred, it may be assumed that further pressure pulses will not be sensed and consequently, the count then stored in the diastolic counter 302 is representative of the final, or lowest, cuff pressure corresponding to the patient's diastolic pressure. A suitable display actuating signal then may be applied to the diastolic display 304.

In the illustrated embodiment, the flip-flop circuits 242 and 262 are selectively energized in timed synchronization with the pulses produced by the clock circuit 210. This is to ensure that, as described above, a fully sampled portion of the pulse train produced by the pulse train gating circuit 206 is transmitted to the respective counters 282 and 302. It is recognized that erroneous pressure displays will be indicated if only a portion of the sampled pulse train is counted. Nevertheless, it should be fully appreciated that this synchronization of the flip-flop circuits 242 and 262, and the respective enabling of the AND-gates 246 and 266 do not affect the accuracy of the pressure indications provided by the displays 286 and 304. This will now be explained.

The flip-flop circuit 242 is capable of being reset to its "reset" state either at the occurrence of a clock pulse trailing edge in the event that the first pressure pulse is sensed during a clock pulse interval T, or immediately upon the occurrence of a pressure pulse if that pressure pulse is sensed during a negative portion of the clock cycle. This latter case is represented by the occurrence of the first pressure pulse 314. This pulse 314 causes the flip-flop circuit 226 to be set to its "set" state, as shown by the broken line in FIG. 3F, resulting in a negative pulse produced by the OR circuit 228, as shown by the broken line in FIG. 3G. As is understood, this negative pulse has the effect of resetting the flip-flop circuit 242 to its "reset" state, as shown by the broken line in FIG. 3H. If the flip-flop circuit 242 is reset during the negative portion of a clock cycle, it is appreciated that the immediately preceding sampled pulse train which had been supplied through the enabled AND-gate 246 to the systolic counter 282 is maintained in that counter, and is not changed. Therefore, if the first pressure pulse occurs during the negative portion of a clock cycle, the maximum change in the cuff pressure which can occur between the time that the systolic counter 282 is incremented and the time that the first pressure pulse is sensed is limited to that change which occurs during the negative portion of a clock cycle. For a duty cycle of 50 percent, it is appreciated that this maximum change in cuff pressure is limited to a time change T. Similarly, and as described hereinabove, if the first pressure pulse occurs during a positive clock pulse, the maximum error in the cuff pressure indication is limited to the change in cuff pressure between the time of occurrence of the pressure pulse and the time of resetting the flip-flop circuit 242. This maximum interval also is equal to T.

Now, if the clock circuit 210 operates at a low frequency of, for example, 5Hz, then T is equal to 0.1 second. In general, the occluding cuff 10 is deflated at the rate of 2—4mm Hg per second. Consequently, the maximum systolic pressure error is seen to be equal to 0.4mm Hg. In comparison with conventional techniques and prior devices which had been used for measuring blood pressure, this maximum error is negligible.

With respect to the maximum error in the indicated diastolic pressure, it is appreciated that the final pressure pulse 312 can occur immediately following the trailing edge of a clock pulse. Hence, it is possible that a complete clock period equal to 2T can be present between the occurrence of the pressure pulse 312 and the transmission to the diastolic counter 302 of the last pulse included in the sampled pulse train. Consistent with the aforedescribed numerical example, the maximum change in the cuff pressure during this time period of 0.2 second is equal to 0.8mm Hg. This maximum error in the diastolic pressure indication is negligible when compared to conventional techniques and prior devices which have been used for such measurements.

Therefore, it is seen that the present invention provides a blood pressure measurement having an accuracy within 1mm Hg of the patient's pressure.

Preferred embodiments of particular portions of the apparatus shown and described with reference to FIG. 2 now will be discussed. In one embodiment of the present invention, the systolic and diastolic displays each are formed of multi-digit conventional seven-segment light-emitting elements. These display elements, which may be used to indicate pressure as measured in millimeters mercury, may comprise light-emitting diodes (LED's), liquid crystal elements, gas discharge elements, and the like. It is known that the use of a seven-segment element requires a display driver which normally is responsive to a 4-bit BCD signal to selectively energize the appropriate segments in the element. For a three-digit pressure indication, three independent display drivers must be used. Thus, in the present invention, if separate systolic and diastolic displays are to be provided, it is appreciated that six display drivers must be used. However, the cost of the display is determined, to a great extent, by the number of display drivers which are necessary. Accordingly, in accordance with one embodiment of this invention, the cost of the display device can be significantly reduced if a single display driver is used to drive all of the display elements included in the systolic and diastolic displays. The logic circuitry which is used in conjunction with a single display driver is shown in FIG. 4.

Essentially, the logic circuit of FIG. 4 is a simplified multiplexing circuit wherein each digit representation stored in the systolic and diastolic counters of FIG. 2 are applied, in multiplexed format, to a single display driver 430, and the output of this display driver is supplied to all of the seven-segment elements, also in multiplexed form. As shown, the systolic counter 282 is comprised of three decade counters 402, 404 and 406 which store digital representations corresponding to the units, tens and hundreds, respectively, of millimeters mercury of pressure. Thus, in response to the sampled pulse train applied thereto, the decade counter 402 essentially counts from 0 to 9 and, upon completing this cycle, increments the decade counter 404. The decade counter 404 is adapted to count from 10 to 90 and, upon completing this cycle, increments the decade counter 406. The decade counter 406 is adapted to count from 100 to 900. It is appreciated that decade counters, as used in this manner, are conventional.

Each decade counter provides a 4-bit code corresponding to the count therein. This is the conventional BCD code wherein each decimal digit is represented by a particular combination of four binary signals. The 4-bit signals produced by the decade counters 402, 404 and 406 are supplied to a single display driver 430 via respective gate circuits 403, 405 and 407. These gate circuits may comprise conventional AND-gates, each receiving one of the bits produced by the corresponding decade counter. Moreover, the gate circuits 403, 405 and 407 are adapted to be sequentially enabled in response to multiplex timing signals applied thereto. To this effect, a multiplex counter 422 is supplied with multiplex timing pulses produced by a multiplex clock circuit 420. It is appreciated that the multiplex counter 422 may comprise a conventional ring counter or, as will become apparent, a conventional count-to-six counter. The first three output terminals, or stages, of the multiplex counter 422 are coupled to the respective gate circuits 403, 405 and 407.

The diastolic counter 302 is substantially similar to the aforedescribed embodiment of the systolic counter 282 and, therefore, may comprise three decade counters 412, 414 and 416, as shown. The 4-bit output signals produced by the respective decade counters are supplied to the display driver 430 via corresponding gate circuits 413, 415 and 417. These gate circuits are similar to the aforedescribed gate circuits 403, 405 and 407 and, as shown, are coupled to the last three output terminals, or stages, of the multiplex counter 422. As is appreciated, when the multiplex counter 422 is incremented in response to the multiplex timing pulses applied by the multiplex clock circuit 420, the gates 403, 405, 407, 413, 415, and 417 are enabled, in sequence. Following the enabling of the gate circuit 417, the cycle repeats and the gate circuit 403 is enabled.

Each seven-segment array included in the three digit display member 440 and the three digit display member 450 is connected in common to the single display driver 430. In one embodiment of the illustrated display members, a seven-segment array is not capable of being energized unless a corresponding actuating transistor coupled thereto is actuated. For this purpose, each seven-segment array included in the display member 440 is coupled to a corresponding actuating transistor 442, 444 and 446, respectively. Similarly, each seven-segment array included in the display member 450 is coupled to a corresponding actuating transistor 452, 454 and 456, respectively. These transistors are coupled to corresponding output terminals, or stages, of the multiplex counter 422, as illustrated.

The operation of the multiplex display apparatus now will be described. Let it be assumed that the display member 440 corresponds to the systolic display and that the display member 450 corresponds to the diastolic display. Let it be further assumed that the decade counters 402, 404 and 406 store the patient's systolic pressure measurement in units, tens and hundreds of millimeters mercury, respectively; and that the decade counters 412, 414 and 416 store the patient's diastolic pressure measurement in units, tens and hundreds of millimeters mercury, respectively. These stored measurement representations are, of course, in digital form. Now, when the first output terminal, or output stage, of the multiplex counter 422 is supplied with a binary "1", only the gate circuit 403 is energized. This permits the units digit stored in the decade counter 402 to be transmitted to the display driver 430. Consequently, all of the seven-segment arrays included in the systolic display 440 and in the diastolic display 450 will be supplied with signals tending to cause the units digit of the systolic pressure measurement to be displayed. However, at this time, only the actuating transistor 446 is actuated. Consequently, only the units digit of the systolic display member 440 will indicate the units digit of the measured pressure.

When the next, or second, output terminal, or stage, of the multiplex counter 422 is energized, only the gate circuit 405 will be enabled to transmit the tens digit representation to the display driver 430. Hence, at this time, all of the seven-segment arrays will be supplied with signals tending to display the tens digit representation of the measured pressure. However, when the second output terminal, or stage, of the multiplex counter 422 is energized, only the actuating transistor 444 will be actuated. Thus, only the tens display array in the systolic display member 440 will be actuated.

It is appreciated that, as the multiplex counter 422 is incremented, the next gate circuit 407, followed, in sequence, by the gate circuits 413, 415 and 417 will be energized. At the same time, the hundreds actuating transistor 442, followed by the units, tens and hundreds actuating transistors 456, 454 and 452, respectively, will be sequentially actuated. Thus, the systolic display member 440 will be actuated to display, in sequence, the units, tens and hundreds digits of the measured systolic pressure. Following this actuation of the systolic display member 440, the diastolic display member 450 will be actuated to display, in sequence, the units, tens and hundreds digits of the diastolic pressure. Thus, only a single display driver 430 need be used, with a resultant saving in cost.

It may be appreciated that, depending upon the multiplex clock circuit frequency, the sequential actuation and display of the respective digits in the systolic and diastolic display members will not be perceived if a sufficiently high clock frequency is used. That is, the cycle of the multiplex counter 422 may be suitably selected so that the human eye will not perceive any flicker.

A preferred embodiment of the pulse train gating circuit 206 now will be described with reference to FIG. 5. It is recalled that the duration of the clock pulses produced by the clock circuit 210 and shown in FIG. 3D is equal to T. Let it be assumed that, during a sampling interval equal to T, it is desired to transmit N pulses, where N equals KP, P being the cuff pressure, in millimeters mercury, and K being an integral proportionality constant. It is also recalled that even if the cuff pressure is reduced to zero, the voltage controlled oscillating circuit 204 nevertheless produces $n$ pulses per second, designated hereinabove as the zero offset pulses. In view of these assumed parameters, the voltage controlled oscillating circuit 204 is assumed to exhibit a pulse repetition rate equal to $(N+n/T)$. The pulse train gating circuit shown in FIG. 5 is adapted to sample this pulse train at periodic intervals throughout a sampling time equal to T and, moreover, to subtract $n$ pulses from the sampled pulse train.

The sampling circuit is comprised of an AND-gate 506 having a first input coupled to the voltage controlled oscillating circuit 204 and a second input coupled to the clock circuit 210. It is appreciated that the AND-gate 506 is periodically enabled for an enabling duration T during which $N+n$ pulses are transmitted. The output terminal of the AND-gate 506 is coupled to a pulse subtracting circuit comprised of an AND-gate 502, a counter 504 and an AND-gate 508. This pulse subtracting circuit is adapted to subtract $n$ pulses from the sampled pulse train.

The counter 504 is a conventional counting circuit and is adapted to be incremented in response to input pulses applied thereto until a predetermined count $n$ is attained. Moreover, the counter 504 is adapted to be reset to an initial, or zero, count upon the occurrence of the leading edge of a clock pulse. Hence, as shown, the voltage controlled oscillating circuit 204 is coupled to the counter 504 via the AND-gate 502, and the reset terminal of the counter is coupled to the clock circuit 210. The output terminal of the counter 504 provides a binary "1" when the count $n$ is reached. As shown, the counter output terminal is coupled to the AND-gate 502 via an inverting circuit 505 and, additionally, is coupled to the AND-gate 508.

In operation, the counter 504 is reset at the commencement of a clock pulse duration in response to the leading edge of the clock pulse. At the same time, the AND-gate 506 is enabled to transmit the pulse train produced by the voltage controlled oscillating circuit 204 to the AND-gate 508. However, since the counter 504 has been reset, the AND-gate 508 now is disabled.

The pulses produced by the voltage controlled oscillating circuit 204 are supplied through the enabled AND-gate 502 to the counter 504 to thus increment the counter. After the first $n$ pulse have been transmitted to the counter and, concurrently, to the AND-gate 508, the counter 504 reaches the count $n$ to thus produce a binary "1". This signal enables the AND-gate 508 to now transmit the remainder of the pulse train produced by the voltage controlled oscillating circuit 204 for the remainder of the clock pulse interval T. At the same time, this binary "1" is inverted by the inverting circuit 505 to disable the AND-gate 502. Consequently, the counter 504 no longer is incremented.

At the conclusion of the clock pulse interval T, the AND-gate 506 is disabled. Thus, it is seen, that the illustrated pulse train gating circuit is effective to periodically sample the pulse train produced by the voltage controlled oscillating circuit 204 and to subtract the zero offset pulses therefrom.

While the present invention has been described with reference to preferred embodiments thereof, it should be particularly understood that various changes in form and details are envisaged. The numerical examples have been discussed by way of example only and should not be interpreted as limiting the present invention thereto. Also, it is contemplated that various changes can be made to the logic circuits which have been described hereinabove. For example, conventional NAND/NOR circuits, or their equivalent, can be used. The particular polarities and representations of the various binary signals likewise can be modified. Furthermore, it should be appreciated from the above discussion that the respective flip-flop circuits are of the so-called positive edge triggering type. That is, the state assumed by such a flip-flop circuit is changed in response to the positive transition of a triggering signal applied thereto. Of course, if desired, these flip-flop circuits can be of the negative edge triggering type.

Although a relatively simple circuit has been described for selectively actuating the flip-flop circuits 242 and 262, it is recognized that various alternative actuating circuits can be used for the purpose of resetting the flip-flop circuit 242 in response to the first-sensed pressure pulse and for preventing the further setting of the flip-flop circuit 262 following the finally-sensed pressure pulse. Also, although the systolic and diastolic counters of FIGS. 2 and 4 have been conveniently described with reference to decade counter circuits, it is appreciated that any other conventional counting circuit can be used, if desired.

Therefore, it is intended that the appended claims be interpreted as including the foregoing and various other changes and modifications in form and details which may be made without departing from the spirit and scope of the invention.

What is claimed is:

1. A sphygmomanometer having an inflatable occluding cuff to be applied to a patient, comprising:
a pressure transducer in fluid communication with said cuff for producing an analog electrical quantity representative of the actual pressure in said cuff and for superposing electrical pulses on said analog quantity in response to pressure pulsations during cardiac cycles of said patient;
converting means electrically coupled to said pressure transducer to convert said analog quantity to a digital representation of the cuff pressure;
pulse detecting means electrically coupled to said pressure transducer for detecting said superposed electrical pulses;
systolic signal producing means coupled to said pulse detecting means for producing a signal representing the systolic pressure of said patient by sensing the first pulse which is detected when said cuff pressure is reduced from a maximum value;
diastolic signal producing means coupled to said pulse detecting means for producing a signal representing the diastolic pressure of said patient by sensing the final pulse which is detected when said cuff pressure is further reduced; and
display means coupled to said converting means for displaying said digital representation when said systolic pressure representing signal is produced by said systolic signal producing means, and for displaying said digital representation when said diastolic pressure representing signal is produced by said diastolic signal producing means;
the said display means comprises:
systolic pressure storage means for storing a digital representation of systolic pressure in the form of a multi-digit number;
a first multi-digit visual display for displaying the multi-digit number representing systolic pressure;

diastolic pressure storage means for storing a digital representation of diastolic pressure in the form of a multi-digit number;

a second multi-digit visual display for displaying the multi-digit number representing diastolic pressure;

a display driver coupled to said first and second multi-digit visual displays for driving the respective visual displays; and multiplex means interconnected between said systolic pressure storage means and said diastolic pressure storage means and said display driver for sequentially supplying said display driver with each digit of the multi-digit numbers stored in said systolic and diastolic pressure storage means.

* * * * *